United States Patent
Wasnik et al.

(10) Patent No.: US 10,621,304 B2
(45) Date of Patent: Apr. 14, 2020

(54) MEDICAL DEVICE CONTROL IN TELEHEALTH SYSTEMS

(71) Applicants: Pankaj Wasnik, Maharashtra (IN); Maharsh Kapadia, Bangalore (IN); Vipin Namboodiri, Karnataka (IN)

(72) Inventors: Pankaj Wasnik, Maharashtra (IN); Maharsh Kapadia, Bangalore (IN); Vipin Namboodiri, Karnataka (IN)

(73) Assignee: Ricoh Co., Ltd., Tokyo (JP)

( * ) Notice: Subject to any disclaimer, the term of this patent is extended or adjusted under 35 U.S.C. 154(b) by 306 days.

(21) Appl. No.: 15/452,549

(22) Filed: Mar. 7, 2017

(65) Prior Publication Data

US 2018/0262550 A1   Sep. 13, 2018

(51) Int. Cl.
| | |
|---|---|
| *H04L 29/06* | (2006.01) |
| *H04L 29/08* | (2006.01) |
| *G06F 19/00* | (2018.01) |
| *G16H 80/00* | (2018.01) |
| *G16H 40/67* | (2018.01) |

(52) U.S. Cl.
CPC ......... *G06F 19/3418* (2013.01); *G16H 40/67* (2018.01); *G16H 80/00* (2018.01); *H04L 65/1063* (2013.01); *H04L 65/607* (2013.01); *H04L 67/12* (2013.01); *H04L 67/02* (2013.01)

(58) Field of Classification Search
CPC ............. G06F 19/3418; H04L 65/1063; H04L 65/607; H04L 65/608; H04L 67/02; H04L 67/12; G16H 80/00; G16H 40/67
See application file for complete search history.

(56) References Cited

U.S. PATENT DOCUMENTS

| | | | | |
|---|---|---|---|---|
| 5,740,801 | A  * | 4/1998 | Branson | G06F 19/321 |
| | | | | 128/920 |
| 7,590,550 | B2 | 9/2009 | Schoenberg | |
| 7,849,184 | B1 * | 12/2010 | Kahn | G06F 11/3055 |
| | | | | 709/224 |
| 8,788,683 | B2 * | 7/2014 | Ball | H04L 65/605 |
| | | | | 709/227 |
| 9,471,515 | B2 * | 10/2016 | Gao-Saari | G06F 13/102 |
| 9,619,849 | B2 * | 4/2017 | Rock | G06Q 10/103 |
| 9,641,432 | B2 * | 5/2017 | Jha | H04L 45/74 |
| 9,849,364 | B2 * | 12/2017 | Tran | H04L 67/12 |
| 9,971,871 | B2 * | 5/2018 | Arrizza | G06F 8/65 |
| 10,042,986 | B2 * | 8/2018 | Ruchti | G06F 19/3468 |

(Continued)

FOREIGN PATENT DOCUMENTS

JP   2014-502172   1/2014

OTHER PUBLICATIONS

Office Action for JP Application No. 2018-014534 and translation, dated Dec. 25, 2018, 7 pgs.

*Primary Examiner* — Kostas J Katsikis
(74) *Attorney, Agent, or Firm* — Patent Law Works LLP

(57) ABSTRACT

A system including one or more processors and a memory. The memory stores instructions that, when executed by the one or more processors, cause the system to receive, via a server, a first real time messaging protocol message from a hub application, the first real time messaging protocol message to control a medical; transmit a device driver command to control the medical device based on the first real time messaging protocol message; receive data from the medical device; and transmit, via the server, the data from the medical device to the hub application.

20 Claims, 7 Drawing Sheets

(56) References Cited

U.S. PATENT DOCUMENTS

| | | | |
|---|---|---|---|
| 10,238,799 B2* | 3/2019 | Kohlbrecher | G06F 19/3468 |
| 10,238,801 B2* | 3/2019 | Wehba | G16H 50/20 |
| 10,242,060 B2* | 3/2019 | Butler | G06Q 10/06 |
| 10,311,972 B2* | 6/2019 | Kohlbrecher | G06F 11/3409 |
| 10,314,974 B2* | 6/2019 | Day | A61M 5/1723 |
| 10,429,810 B2* | 10/2019 | Edelen | G05B 19/042 |
| 10,434,246 B2* | 10/2019 | Silkaitis | G06Q 50/00 |
| 2007/0055799 A1* | 3/2007 | Koehler | G16H 40/63 710/62 |
| 2008/0294490 A1* | 11/2008 | Nuhaan | G06Q 10/06311 705/7.15 |
| 2009/0112630 A1* | 4/2009 | Collins, Jr. | G06F 19/3418 705/3 |
| 2010/0169635 A1* | 7/2010 | Chinnaswamy | G06F 21/57 713/2 |
| 2010/0306365 A1* | 12/2010 | Gale | H04L 51/14 709/224 |
| 2011/0107225 A1* | 5/2011 | Sukanen | H04L 67/02 715/736 |
| 2011/0167250 A1* | 7/2011 | Dicks | A61B 5/1112 713/2 |
| 2011/0179405 A1* | 7/2011 | Dicks | G06F 8/61 717/168 |
| 2011/0264463 A1* | 10/2011 | Kincaid | G06F 3/0488 705/3 |
| 2012/0182939 A1* | 7/2012 | Rajan | A61B 5/0008 370/328 |
| 2013/0163580 A1* | 6/2013 | Vass | H04L 65/104 370/352 |
| 2013/0211265 A1* | 8/2013 | Bedingham | G06F 19/3418 600/483 |
| 2014/0019149 A1* | 1/2014 | Yu | G16H 80/00 705/2 |
| 2014/0073880 A1* | 3/2014 | Boucher | A61B 1/227 600/301 |
| 2014/0195675 A1* | 7/2014 | Silver | H04L 65/1083 709/224 |
| 2014/0207486 A1* | 7/2014 | Carty | G06Q 50/22 705/2 |
| 2014/0365240 A1* | 12/2014 | Canton | G06Q 50/22 705/3 |
| 2014/0366878 A1* | 12/2014 | Baron | A61B 5/4836 128/204.23 |
| 2015/0127381 A1* | 5/2015 | Vo | G06F 19/3418 705/3 |
| 2015/0363562 A1* | 12/2015 | Hallwachs | G06F 19/321 705/3 |
| 2016/0026763 A1* | 1/2016 | Reddy | H04M 3/42059 379/265.09 |
| 2016/0232010 A1* | 8/2016 | Dicks | G06F 8/654 |
| 2016/0364541 A1* | 12/2016 | Flippen | G06F 19/3418 |
| 2017/0048292 A1* | 2/2017 | Lee | H04L 65/4076 |
| 2017/0098051 A1* | 4/2017 | Balram | G16H 10/60 |
| 2017/0180453 A1* | 6/2017 | Lee | H04L 61/2007 |
| 2017/0262599 A1* | 9/2017 | Grisel | G16H 50/20 |
| 2017/0325786 A1* | 11/2017 | Pepe | H04L 65/4069 |
| 2017/0329922 A1* | 11/2017 | Eberting | G06F 19/3418 |
| 2017/0364653 A1* | 12/2017 | Wong | G06F 19/3418 |
| 2017/0371932 A1* | 12/2017 | Chamarajnagar | G06F 7/20 |
| 2018/0032692 A1* | 2/2018 | Hickle | G06F 19/3418 |
| 2018/0052968 A1* | 2/2018 | Hickle | H04M 3/5116 |
| 2018/0336500 A1* | 11/2018 | Pinho | G16H 10/40 |

\* cited by examiner

US 10,621,304 B2

MEDICAL DEVICE CONTROL IN TELEHEALTH SYSTEMS

BACKGROUND

The present disclosure relates to telehealth. In particular, the present disclosure relates to medical device control in a telehealth system. Remote healthcare, and in particular telehealth, is an emerging area of contemporary healthcare. Telehealth is the delivery of health-related services and information via telecommunications technologies. Telehealth may allow a patient to be monitored between physician office visits which can improve patient health. Telehealth may also allow patients to access expertise which is not available in their local area.

SUMMARY

The present disclosure relates to medical device control in a telehealth system. According to one innovative aspect of the subject matter in this disclosure, a system includes one or more processors and a memory. The memory stores instructions that, when executed by the one or more processors, cause the system to receive a first real time messaging protocol message from an application, the first real time messaging protocol message to control a medical device; transmit a device driver command to control the medical device based on the first real time messaging protocol message; receive data from the medical device; and transmit the data from the medical device to the application.

Other implementations of one or more of these aspects include corresponding systems, methods, apparatus, and computer programs, configured to perform the actions of the methods, encoded on computer storage devices.

It should be understood that language used in the present disclosure has been principally selected for readability and instructional purposes, and not to limit the scope of the subject matter disclosed herein.

BRIEF DESCRIPTION OF THE DRAWINGS

The present disclosure is illustrated by way of example, and not by way of limitation in the figures of the accompanying drawings in which like reference numerals are used to refer to similar elements.

DETAILED DESCRIPTION

An important aspect of patient care in telehealth applications is the ability to interact with various medical devices (e.g., blood pressure meters, spirometers, heart rate meters, etc.). Further, to reduce chances of human error, the telehealth systems is capable of accessing the medical data generated by the various medical devices. Current systems are limited in the ability to effectively serve patient needs. The telehealth system disclosed herein provides medical device control that is capable of connecting with a full range of devices over several input and output (I/O) interfaces. For example, the technology can use universal serial bus (USB), Bluetooth, RS-232, The Institute of Electrical and Electronics Engineers' (IEEE) 802.3 Ethernet, IEEE's 802.11 wireless local area network (WLAN), high-definition multimedia interface (HDMI), video graphics array (VGA), component video interface, composite video interface, audio interfaces, etc.

In general, the technology disclosed herein is interface agnostic and vendor neutral. Further, the technology can reproduce device specific workflows (e.g., a spirometer workflow including pre and post dilation, a blood pressure workflow, etc.). Currently available techniques to control devices with a web browser include the Netscape plugin application programming interface (NPAPI), the native client (NaCl) based plugins available on some notable web browsers, and representational state transfer (REST) through a web server.

Figure 1:
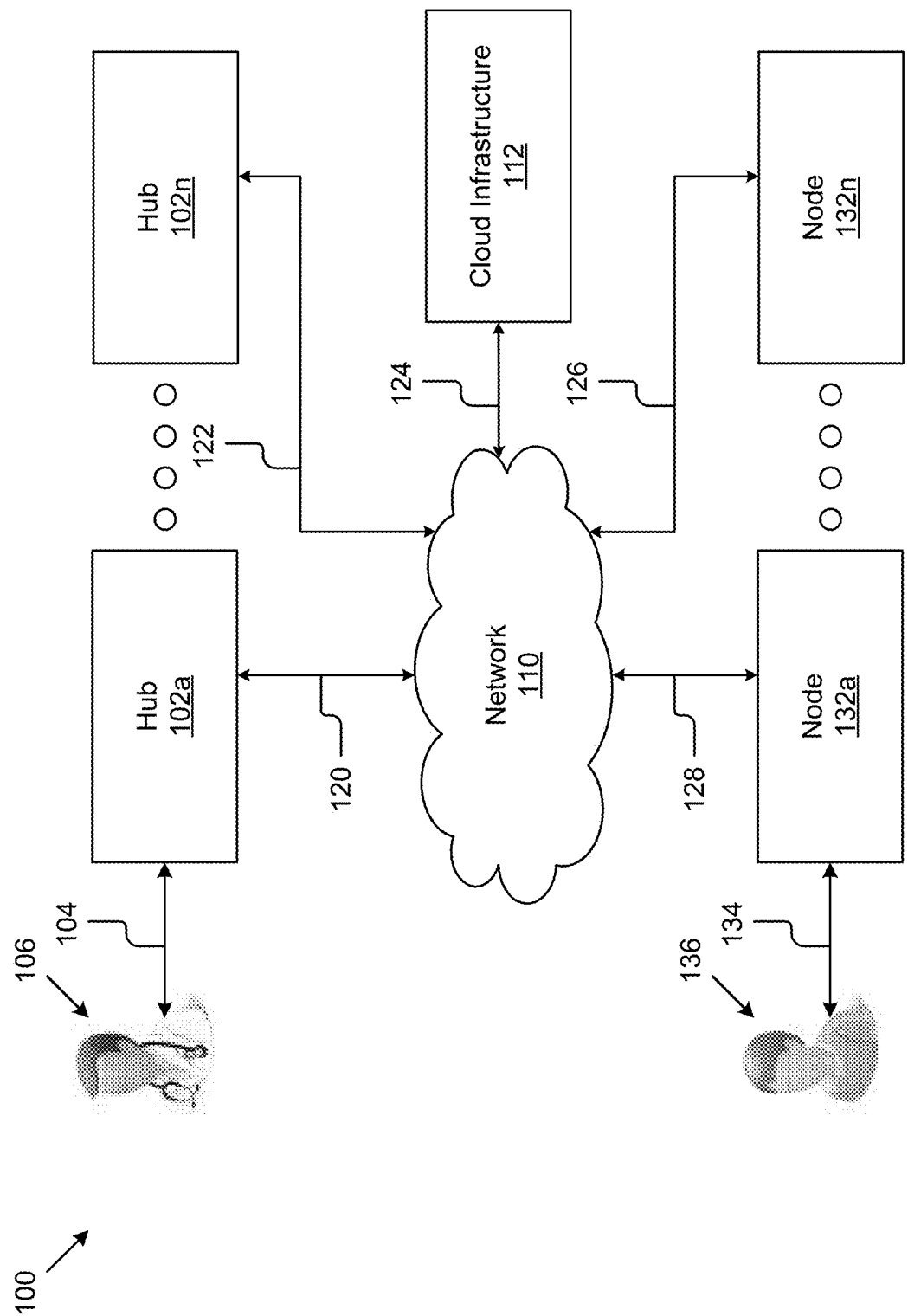
FIG. 1 depicts a high-level block diagram illustrating an example system for implementing medical device control in a telehealth system according to the techniques described herein.

FIG. 1 depicts a high-level block diagram illustrating an example system 100 for implementing medical device control in a telehealth system. The system includes one or more hubs 102, a cloud infrastructure 112, and one or more nodes 132 communicatively connected through a network 110. Thus, in the illustrated embodiment, the hub 102a, a cloud infrastructure 112, and the node 132a are communicatively coupled respectively via signal lines 120, 124, and 128 to the network 110. Further, other hubs and nodes, such as hub 102n and node 132n, may be communicatively coupled via signal lines 122 and 126. However, the present disclosure is not limited to this configuration and a variety of different system environments and configurations can be deployed and are within the scope of the present disclosure. Other embodiments may include additional or fewer components. For example, the cloud infrastructure 112 may include multiple instances located at various remote locations.

It should be recognized that FIG. 1 as well as the other figures used to illustrate an embodiment and an indication of a letter after a reference number or numeral, for example, "102a," is a specific reference to the element or component that is designated by that particular reference numeral. In the event a reference numeral appears in the text without a letter following it, for example, "102," it should be recognized that such is a general reference to different embodiments of the element or component bearing that general reference numeral.

Control messages may be communicated from the hub 102 to the node 132 via a centralized event management server, such as cloud infrastructure 112. Communication via the centralized event management server in the event of intermittent network faults to either the node or the hub is consistent since the last sent message may persist at the centralized event management server.

The hub 102 includes facilities used (as indicated by use line 104) by a doctor 106, or another healthcare professional who may diagnose patients and provide medical care. In particular, the hub 102 may implement, in part, medical device control. The hub 102 may include computing hardware, input devices, display devices and other output devices. The hub 102, may include a non-transitory computer-usable (e.g., readable, writeable, etc.) medium, which can be any non-transitory apparatus or device that can contain, store, communicate, propagate or transport instructions, data, computer programs, software, code routines, etc., for processing by or in connection with a processor. The hub 102 may also include various applications. For instance, the hub 102 may include a web browser to access web applications.

The network 110 can be a conventional type, wired or wireless, and may have numerous different configurations including a star configuration, token ring configuration, or other configurations. Furthermore, the network 110 may include a wide area network (WAN) (e.g., the Internet), a local area network (LAN), and/or other interconnected data paths across which multiple devices may communicate. In some instances, the network 110 may be a peer-to-peer network. The network 110 may also be coupled to or includes portions of a telecommunications network for sending data in a variety of different communication protocols. In some instances, the network 110 may be a virtual private network (VPN) operating over one of the aforementioned types of networks.

The cloud infrastructure 112 may be an Internet, or other network-based, computing platform that provides processing resources and data storage for device control and auditing. In particular, the cloud infrastructure may implement, in part, medical device control. The cloud infrastructure 112 may include computing hardware, input devices, display devices and other output devices. The cloud infrastructure 112, may include a non-transitory computer-usable (e.g., readable, writeable, etc.) medium, which can be any non-transitory apparatus or device that can contain, store, communicate, propagate or transport instructions, data, computer programs, software, code routines, etc., for processing by or in connection with a processor. The cloud infrastructure 112 may also include various applications. For instance, the cloud infrastructure 112 may include streaming and messaging protocols (e.g., a real time streaming protocol (RTSP) service 202 and a real time messaging protocol (RTMP) service 204). RTSP and RTMP are used herein as examples of streaming and messaging protocols that are suitable for communication between remote medical devices and/or computing devices at the node 132 and the hub 102 via the cloud infrastructure 112. It should be understood that there are protocols other than RTSP and RTMP that may be suitable for such communication. Information detailing the RTSP service 202 and the RTMP service 204 are described further with reference to FIG. 2 and the remaining figures.

The node 132 includes facilities used (as indicated by use line 134) by a patient and/or a technician 136 to receive telehealth medical care. A technician may physically attend the patient and perform duties such as taking the patient's vitals, and technically assisting the patient in receiving the telehealth medical care through the system 100. The node 132 may implement, in part, medical device control. In some embodiments, control of the medical device may be originated by a technician at the node 132, a doctor at the hub 102, or an application running at the hub 102 or node 132. The node 132 may include computing hardware, input devices, display devices and other output devices. The node 132, may include a non-transitory computer-usable (e.g., readable, writeable, etc.) medium, which can be any non-transitory apparatus or device that can contain, store, communicate, propagate or transport instructions, data, computer programs, software, code routines, etc., for processing by or in connection with a processor. The node 132 may also include various applications. For instance, the node 132 may include a technician application 310 and a device control bus 320. Information detailing the technician application 310 and the device control bus 320 are described further with reference to FIGS. 3 and 4, and the remaining figures.

The doctor 106 may select a medical device to manipulate from an application on the hub 102. In some cases, the application may be web application accessed through a web browser and hosted by a web server. Regardless, when a remote medical device is manipulated in the application, a message may be sent to the node 132 for manipulating a medical device at the node 132. In some embodiments, the medical device at the node 132 may produce a device stream. For example, an otoscope may produce a video device stream. A stethoscope may produce an audio device stream. A magnetic resonance imaging (MRI) scanner may produce an image. A camera may produce a video stream.

In some cases, the message may be transmitted using RTMP and may pass through the cloud infrastructure 112 for audit recording. In some cases, a stream may use RTSP and may pass through the cloud infrastructure 112 for audit recording. In some cases, the cloud infrastructure may implement load balancing to spread utilization of computing resources across multiple servers, sites, and locales.

Figure 3:
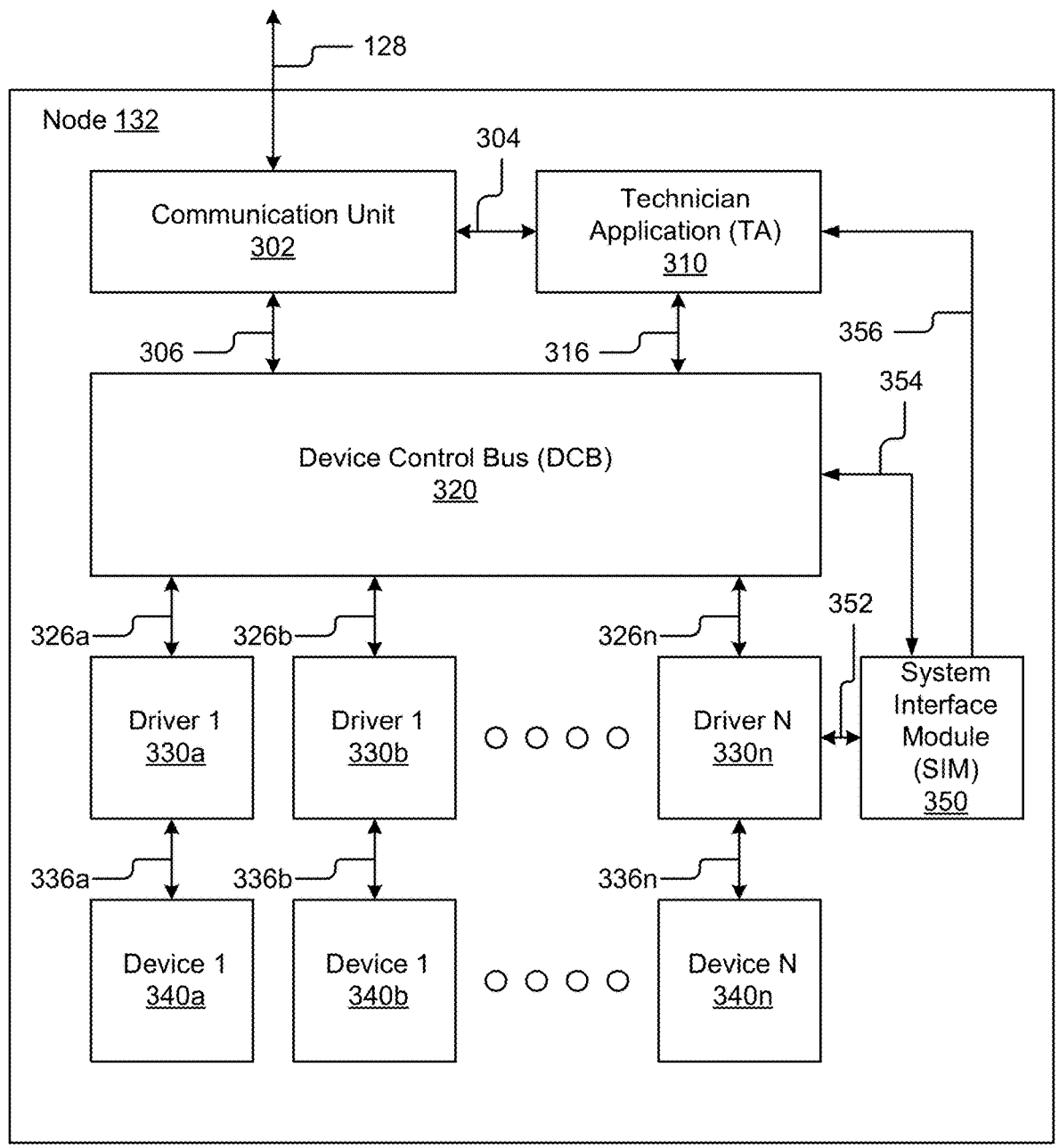
FIG. 3 depicts a block diagram illustrating an example of a node according to the techniques described herein.

The techniques introduced herein may be used to loosely couple a doctor side web application and a technician side web application. In particular, the device control bus 320, discussed with reference to FIG. 3, is an architecture that is capable of providing a secure, seamless, hypertext transfer protocol (HTTP) abstraction layer for a browser based application to communicate with devices connected to the system 100. This technology may also provide a seamless interface for a technician or a node 132 side web application to access various medical devices and record patient vitals data.

Figure 2:
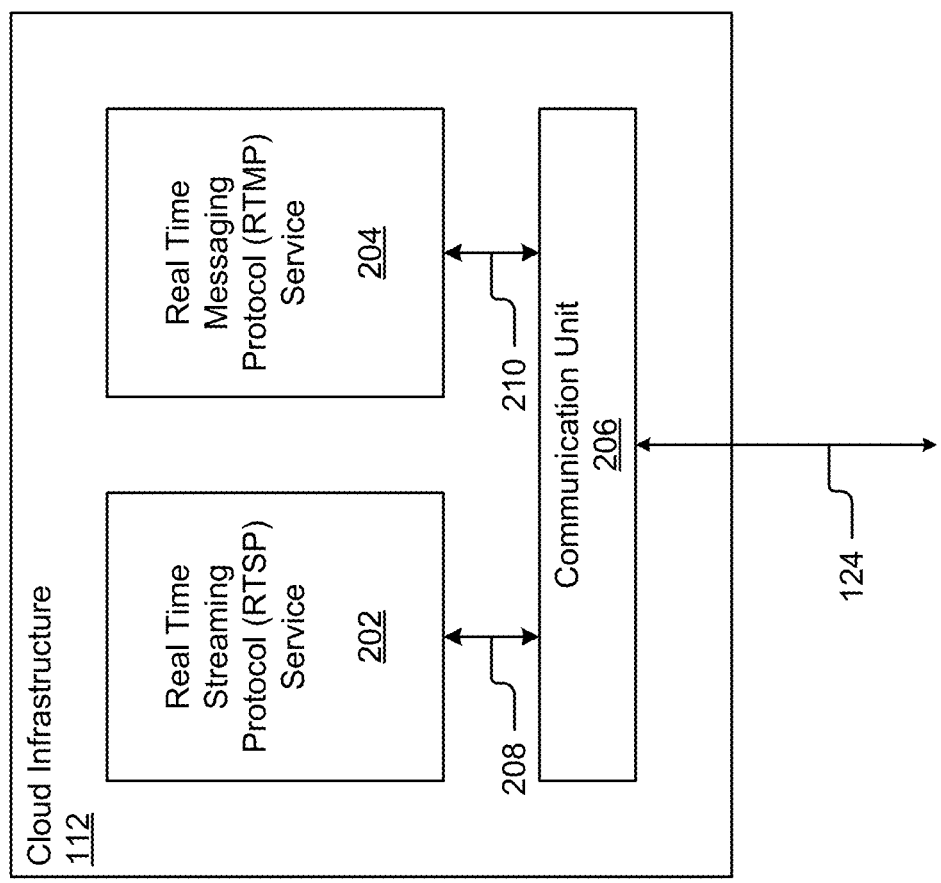
FIG. 2 depicts a block diagram illustrating an example of a cloud infrastructure according to the techniques described herein.

FIG. 2 depicts a block diagram illustrating an example of a cloud infrastructure 112. The cloud infrastructure 112 is combinational logic, firmware, software, code, or routines, or some combination thereof, for implementing, in part, medical device control. As depicted in FIG. 2, the cloud infrastructure may include a RTSP service 202, a RTMP service 204, and a communication unit 206. The RTSP service may be communicatively connected to the communication unit 206 as indicated by the signal line 208. Similarly, the RTMP service 204 may be communicatively connected to the communication unit 206 as indicated by the signal line 210. The communication unit 206 may be communicatively connected to the network 110, described with reference to FIG. 1, as indicated by the signal line 124.

The RTSP service 202 may pass information streams from the node 132 to a hub 102 and provide an audit trail for the telehealth medical care provided over the system 100. The RTSP service 202 may also utilize the real-time transport protocol (RTP) or the hypertext transfer protocol (HTTP) to stream the actual data of the stream, whereas RTSP may be used as a network control protocol to establish and control the media session. In some cases, RTSP may be used on top of a HTTP or a secure HTTP connection. In some instances, JavaScript may receive and implement the RTSP control messages. The RTMP service 204 may pass messages between the node 132 and the hub 102 and provide an audit trail for the telehealth medical care provided over the system 100.

FIG. 3 is a block diagram illustrating an example of a node 132. The node 132 includes a communication unit 302, a technician application 310, a device control bus 320, drivers 330, corresponding medical devices 340, and a system interface module 350.

The communication unit 302 transmits and receives data to and from the network 110. The communication unit 302 is communicatively coupled to the technician application 310 as indicated by the signal line 304 and the device control bus 320 as indicated by the signal line 306. In some instances, the communication unit 302 includes a port for direct physical connection to the network 110 or to another communication channel. For example, the communication unit 302 includes a USB, SD, CAT-5 or similar port for wired communication with the network 110. In some instances, the communication unit 302 includes a wireless transceiver for exchanging data with the network 110 or other communication channels using one or more wireless communication methods, including IEEE 802.11, IEEE 802.16, BLUETOOTH®, cellular communication, or another suitable wireless communication method.

The technician application 310 can be software including routines for interfacing with a technician at the node 132. In some instances, the technician application 310 can be set of instructions executable by a processor to provide functionality described below for interfacing with a technician at the node 132. In some other instances, the technician application 310 may be stored in a memory of the node 132 and can be accessible and executable by the processor. While illustrated in FIG. 3 as being integrated with the node 132, in some cases the technician application 310 may be hosted or accessed through a separate computing device (e.g., as a web application hosted on a web server such a cloud services 112). The technician application 310 allows a technician at a node location to interact with the system in a way similar to the doctor 106 while being locally available to the patient 136.

The device control bus 320 can be software including routines for interfacing with medical devices. In some instances, the device control bus 320 can be set of instructions executable by a processor to provide functionality described below for controlling a device. In some other instances, the device control bus 320 may be stored in a memory of the node 132 and can be accessible and executable by the processor.

The device control bus 320 may receive RTMP messages directing control of a device 340 and may translate the RTMP message to driver commands to pass to the driver 330 of the device 340. Conversely, the device control bus 320 may receive data from the device 340 through the driver 330 which the device control bus 320 can translate to an RTMP message. The device control bus 320 may then transmit the message using the communication unit 302 through the network 110 to the hub 102. Further details of the device control bus 320 are discussed with reference to FIG. 4 and the remaining figures below.

The driver 330 can be software including routines for communicating with a device 340. In some instances, the driver 330 can be set of instructions executable by a processor to provide functionality described below for controlling a device. In some other instances, the driver 330 may be stored in a memory of the node 132 and can be accessible and executable by the processor.

The driver 330 may operate or control a particular type of device 340 that is attached to the node 132. The driver 330 provides a software interface to the hardware device 340, thereby enabling an operating system on the node 132 and other computer programs on the node 132 (e.g., the device control bus 320, the technician application 310, etc.) to access hardware functions of the device 340. For example, the driver 330 may provide for a direct connection between the node 132 and the device 340 to execute commands and/or read results in response to requests from the node. In such an embodiment, the driver 330 may not provide an explicit user interface reflecting the device 340 with which a user interacts. For example, a medical assistant may fill out an intake form using an application at the node 132 and, when the form calls for information regarding the patient's vital signs, the application may initiate a request via the driver 330 to read the patient's vital signs using a thermometer, a blood pressure cuff, a weight scale, a pulse oximeter, etc. and record the results in an intake form. In another embodiment, the driver 330 may generate and present a user interface that represents the medical device 340 and allows a user to control the medical device via the user interface. The driver 330 may communicate with the device 340 through the computer bus or communications subsystem to which the hardware connects, as indicated generally by the signal line 336.

The device 340 may be a medical device may be, but is not limited to, a stethoscope, a blood pressure meter, a pulse oximeter, a thermometer, an ophthalmoscope, a weight and height scale, an otoscope, a camera, a telecardiology device (e.g., an ECG machine), a telepathology device (e.g., a microscope), a teledermatology device (e.g., a high-resolution camera), a teleradiology device (e.g., an ultrasound machine), etc. The devices 340 may be controlled by a remote hub (e.g., during a remote physical examination) or may be controlled based on a defined workflow. In some embodiments, control of the devices 340 originates at the node 132. For example, before the patient is presented to the remote doctor, a workflow may include measurement of vital signs. Devices 340 may be of several types. For example, a command type and a data payload type. A command type device receives a command (e.g., from a hub 102 or node 132 application) and provide a response. Similarly, a command type device may be event driven and monitor applications and/or other devices to provide a response to or forward results from a detected event. A data payload type device may continuously provide a streaming payload (e.g., a scope, camera, or audio feed) or may provide a finite payload (e.g., a measurement from a thermometer). Naturally, a particular device may be of one or more types.

The system interface module 350 provides an interface from the drivers 330 to the device control bus 320 as indicated by the signal line 354 and to the technician application 310 as indicated by the signal line 356 for performing lower level operations such as providing mac address, performing file reads, opening communication ports, and the like. The system interface module 350 directly communicates with devices 340 through device drivers 330, as indicated by signal line 352, to control them as per the request from the hub 102 (e.g., to perform a function requested by a doctor).

Figure 4:
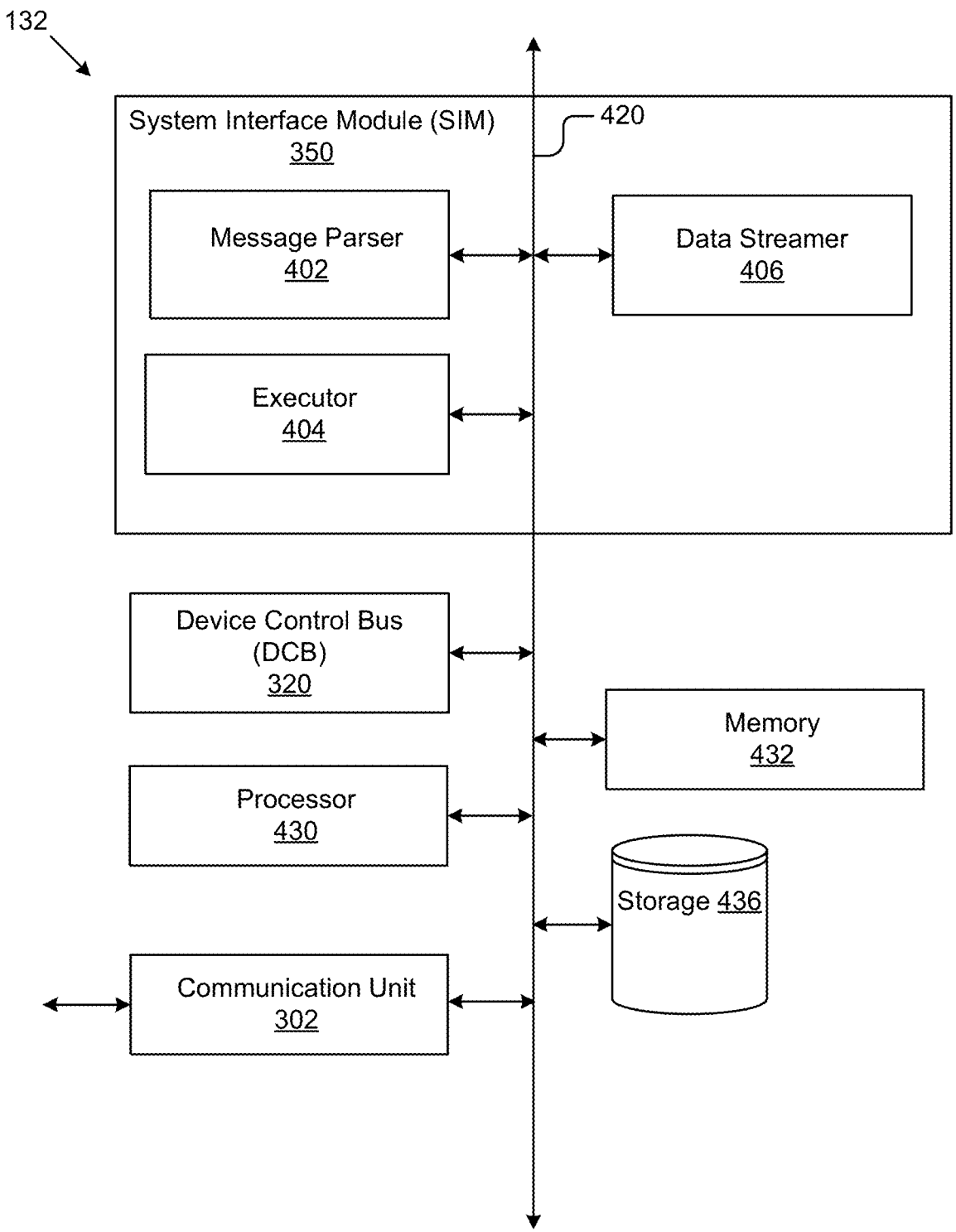
FIG. 4 depicts a block diagram illustrating an example of a device control bus according to the techniques described herein.

FIG. 4 is a block diagram illustrating an example of a node 132 with a system interface module 350. The node 132 includes a system interface module 350, a device control bus 320, a processor 430, a memory 432, a communication unit 302, and a storage device 436. The components of the node 132 are communicatively coupled by a bus 420.

The processor 430 includes an arithmetic logic unit, a microprocessor, a general purpose controller, or some other processor array to perform computations and provide electronic display signals to a display device. The processor 430 is coupled to the bus 420 for communication with the other components of the node 132. Processor 430 processes data signals and may include various computing architectures including a complex instruction set computer (CISC) architecture, a reduced instruction set computer (RISC) architecture, or an architecture implementing a combination of instruction sets. Although FIG. 4 includes a single processor 430, multiple processors 430 may be included. Other processors, operating systems, sensors, displays and physical configurations are possible.

The memory 432 stores instructions and/or data that may be executed by the processor 430. The memory 432 is coupled to the bus 420 for communication with the other components of the node 132. The instructions and/or data stored in memory 432 may include code for performing the techniques described herein. The memory 432 may be a dynamic random access memory (DRAM) device, a static random access memory (SRAM) device, flash memory, or some other memory device. In some instances, the memory 432 also includes a non-volatile memory or similar permanent storage device and media including a hard disk drive, a floppy disk drive, a CD ROM device, a DVD ROM device, a DVD RAM device, a DVD RW device, a flash memory device, or some other mass storage device for storing information on a more permanent basis.

The communication unit 302 transmits and receives data to and from the network 110. The communication unit 302 is coupled to the bus 420. In some instances, the communication unit 302 includes a port for direct physical connection to the network 110 or to another communication channel. For example, the communication unit 234 includes a USB, SD, CAT-5 or similar port for wired communication with the network 110. In some instances, the communication unit 302 includes a wireless transceiver for exchanging data with the network 110 or other communication channels using one or more wireless communication methods, including IEEE 802.11, IEEE 802.16, BLUETOOTH®, cellular communication or another suitable wireless communication method.

The storage 436 can be a non-transitory memory that stores data for providing the functionality described herein. The storage 436 may be a dynamic random access memory (DRAM) device, a static random access memory (SRAM) device, flash memory, or some other memory devices. In some instances, the storage 436 also includes a non-volatile memory or similar permanent storage device and media including a hard disk drive, a floppy disk drive, a CD ROM device, a DVD ROM device, a DVD RAM device, a DVD RW device, a flash memory device, or some other mass storage device for storing information on a more permanent basis.

The system interface module 350 can be software including routines for implementing medical device control. In some instances, the system interface module 350 can be a set of instructions executable by the processor 430 to provide functionality described herein for controlling medical devices. In some other instances, the system interface module 350 may be stored in the memory 432 of the node 132 and can be accessible and executable by the processor 430. The system interface module 350 may be adapted for cooperation and communication with the processor 430 and other components of the node 132 via the bus 420. The system interface module 350 includes a message parser 402, an executor 404, and a data streamer 406.

The message parser 402 can be software including routines for implementing medical device control. In some instances, the message parser 402 can be set of instructions executable by the processor 430 to provide functionality described below for streaming medical information. In some other instances, the message parser 402 may be stored in the memory 432 of the node 132 and can be accessible and executable by the processor 430. The message parser 402 may be adapted for cooperation and communication with the processor 430 and other components of the node 132 via the bus 420. The message parser 402 parses a response from the medical device to read the configuration setting. Likewise, the message parser 402 parses a received RTMP message in order to convert the RTMP message to one or more device driver commands.

The executor 404 can be software including routines for implementing medical device control. In some instances, the executor 404 can be set of instructions executable by the processor 430 to provide functionality described below for streaming medical information. In some other instances, the executor 404 may be stored in the memory 432 of the node 132 and can be accessible and executable by the processor 430. The executor 404 may be adapted for cooperation and communication with the processor 430 and other components of the node 132 via the bus 420. The executor 404 passes or issues commands to the device driver in order to effectuate actions specified in a received RTMP message to control a medical device.

The data streamer 406 can be software including routines for implementing medical device control. In some instances, the data streamer 406 can be set of instructions executable by the processor 430 to provide functionality described below for streaming medical information. In some other instances, the data streamer 406 may be stored in the memory 432 of the node 132 and can be accessible and executable by the processor 430. The data streamer 406 may be adapted for cooperation and communication with the processor 430 and other components of the node 132 via the bus 420. The data streamer 406 receives data from the device driver to stream to the cloud infrastructure 112 using RTSP. In particular, the data streamer 406 sends an RTSP stream to the RTSP service 204 in the cloud infrastructure 112. For example, the data streamer 406 may receive a device-level stream from the device driver and transform the device-level stream into an RTSP stream. In some cases, RTMP messages and RTSP streams may be encrypted and sent to a medical auditing service in the cloud infrastructure 112.

Figure 5:
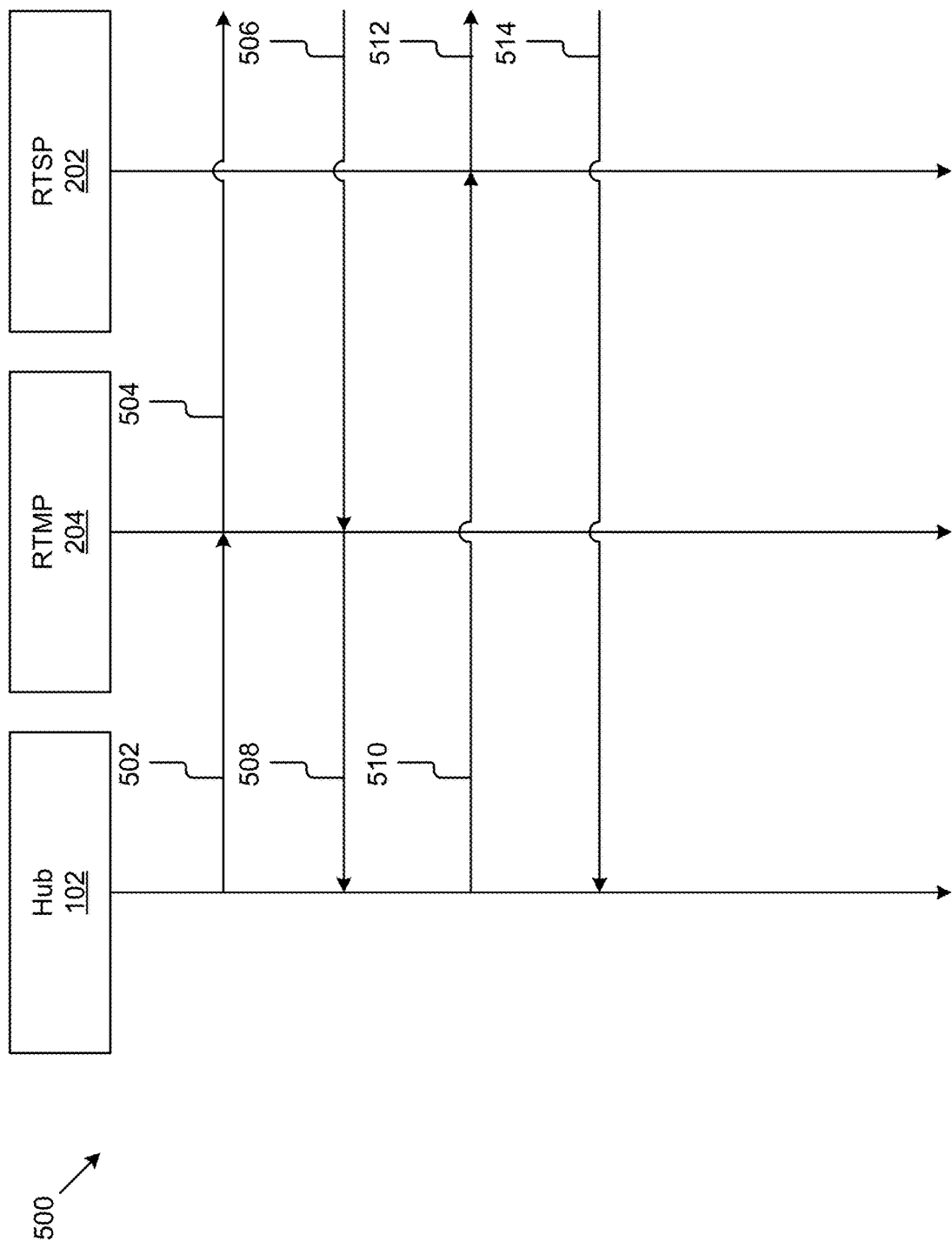
FIGS. 5 and 6 depict flow diagrams of example methods of implementing medical device control in a telehealth system according to the techniques described herein.

FIG. 5 is a flow diagram depicting an example flow 500 for implementing medical device control in a telehealth system. In the flow 500, the hub 102 transmits an RTMP message 502 to the RTSP service 204, which in turn passes the RTMP message onward 504, for example, to the node 132. For example, the RTMP message may be a command to power on a device, read a configuration setting for the device, set a configuration setting for the device, operate the device in a specific way, etc. In some cases, the RTMP service 204 in the cloud infrastructure may record the passing RTMP message and store the RTMP message for medical auditing.

Thus, the node 132 may receive an RTMP message from a hub 102 to control one or more medical devices. Upon receiving the RTMP message 504, the system interface module 350 of the node 132 controls the device specified in the RTMP message 504 by generating one or more device driver commands to control the medical devices based on the RTMP message 504, and returns a feedback RTMP message as indicated by the flow line 506 to the RTMP service 204.

The RTMP service 204 records the RTMP message 506 for auditing purposes and forwards the RTMP message 508 to the hub 102. In the event that the RTMP message 504 effectuated an information stream, the hub 102 sends a request 510 to the RTSP service 202 to request the information stream. The RTSP service 202 transmits the request 512 to the node 132, and the node 132 responds by providing the hub 102 with the information stream 514. In some embodiments, the RTSP service 202 may be bypassed and the system interface module 350 of the node 132 may directly send the stream to the hub 102. In other embodiments, the system interface module 350 may send a copy of the information stream to the hub 102 directly as well as the RTSP service 202 so that the RTSP service 202 can record the information stream for medical auditing purposes.

Medical device control implementations may include specific protocols that address various attributes. For example, one attribute may be a device identifier. Another attribute may be commands such as start, stop, mode of operation (e.g., for a stethoscope may operate in a diaphragm mode, a chest mode, etc.). Start and stop commands may be used to start or stop a device and stream the data or it may be used to start a specific sequence of workflow for a device. For example, with a spirometer, a particular start command may start a flow volume measurement workflow in response to the particular start command. Another attribute may be an authorization token to provide security and indicate that a hub is authorized to control a device at the node. Another attribute may be an address of a server where the node application must post the results.

Figure 6:
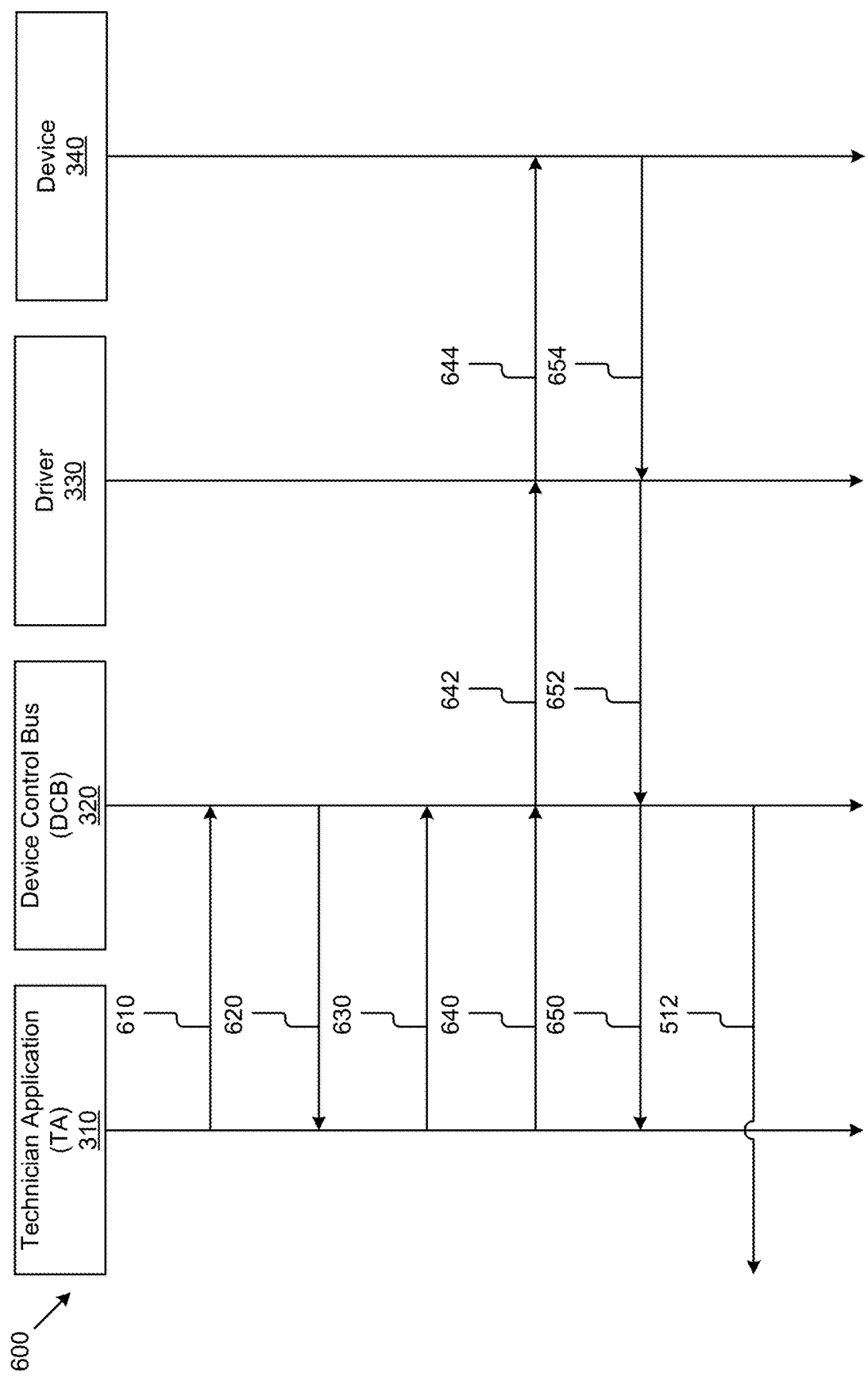

FIG. 6 is a flow diagram depicting an example flow 600 for implementing medical device control in a telehealth system. In the example flow 600, the technician application 310 forwards an RTMP message 610 to the device control bus 320 for reading a configuration of a device attached to the device control bus 320. In some cases, the RTMP message may be sent over an HTTP connection with a POST request. The device control bus 320 returns the configuration 620 of the device for reading by the technician at the technician application 310. The technician application 310 transmits a message 630 to the device control bus 320 to load the device driver. With a request to load a device driver, the device control bus 320 in some cases may provide a response where an issue arises and otherwise may not generate a response.

The technician application 310, for example, in response to an input by a technician, transmits an RTMP message 640 to take a measurement with the device. The device control bus 320 passes the RTMP message 642 to the driver 330, which forwards the message 644 to the device 340. In response to the message 644, the device 340 takes a measurement and transmits the measurement 654 to the driver 330, which passes the message 652 to the device control bus 320. The device control bus 320 passes the message 650 to the technician application 310 where the results of the measurement are displayed to the technician. In some embodiments, the device control bus 320 may also initiate an information stream 512 and transmit the information stream using RTSP to the RTSP service 202 in the cloud infrastructure 112.

Figure 7:
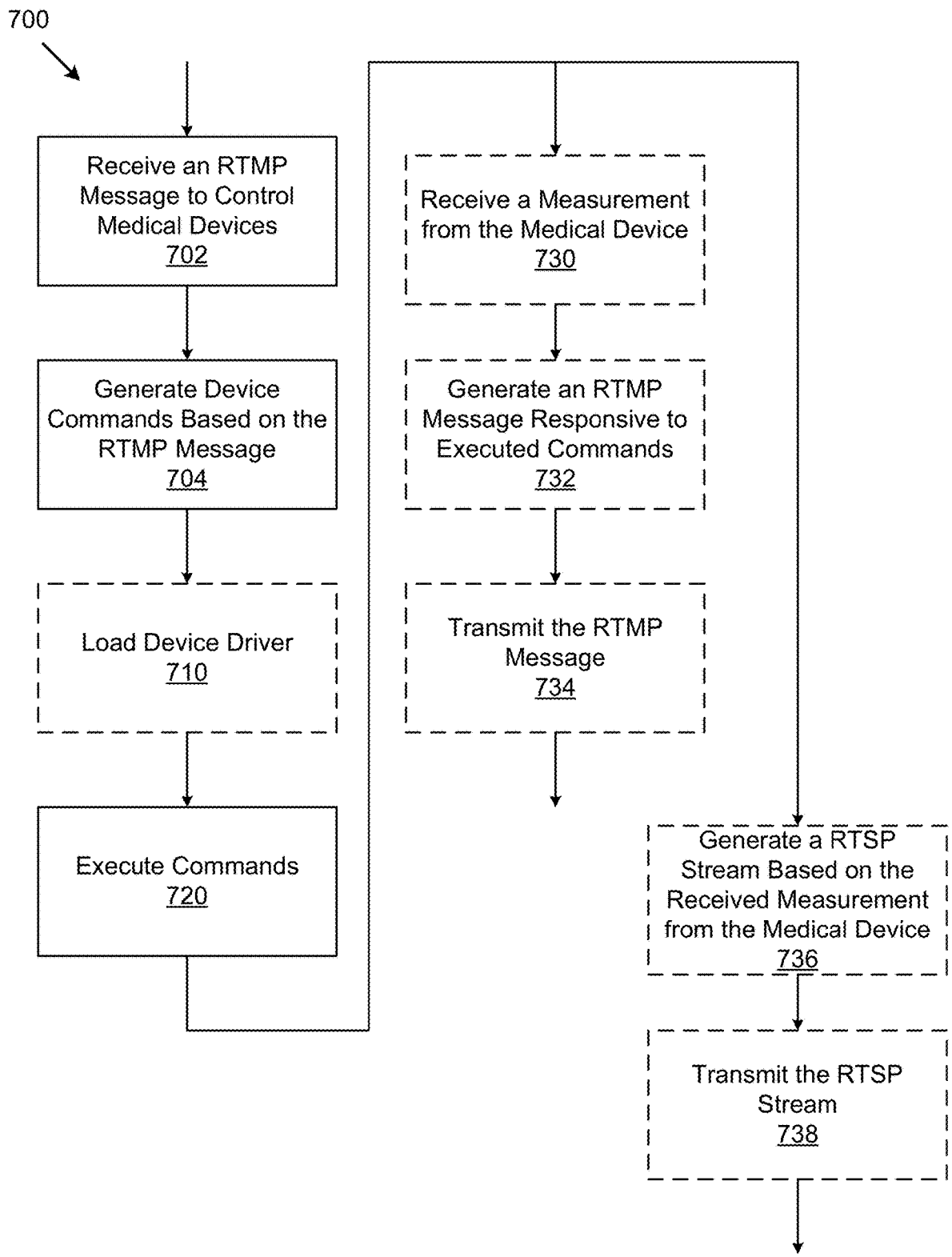
FIG. 7 depicts a flow chart of an example method of medical device control in a telehealth system according to the techniques described herein.

FIG. 7 is a flow chart of an example method 700 of medical device control in a telehealth system. At 702, a node 132 receives an RTMP message to control one or more medical devices 340 attached at the node 132. For example, the node 132, and in particular the device control bus 320, may receive an RTMP from the hub 102 over the network 110. In some embodiments, the RTMP message is generated by a RTMP service in the cloud infrastructure 112. In some cases, the RTMP message may be copied and/or forwarded to the technician application 310 for viewing or interaction by a technician.

At 704, one or more device driver commands may be generated to control the medical devices based on the RTMP message. For example, the message parser 402 may receive the RTMP message and convert each part of the RTMP message to one or more system-level commands.

In some embodiments, at 710, the device control bus determines that a device driver for a medical device has not been loaded and dynamically loads the device driver. At 720, the device driver commands are executed and the device 340 performs the measurement. For example, the system level commands may be passed to the executor 404 which may further convert the system-level commands to device driver commands which the executor 404 then sends to the particular device driver 330. In some embodiments, at 730, the device control bus 320 receives a measurement from a medical device. At 732, the device control bus 320 may generate an RTMP message with results from the measurement and at 734 transmit the RTMP message. For example, the device control bus 320 may transmit the RTMP message to the technician application 310 to be presented to the technician at the node 132. In another embodiment, the device control bus 320 may transmit the RTMP message to the cloud infrastructure 112 to be forwarded to the hub 102 or directly to the hub 102.

In some embodiments, at 736, the device driver transmits the measurements to the system interface module 350 to be forwarded to the real time streaming protocol service 202 of the cloud infrastructure 112 where an RTSP stream is generated based on the received measurement from the medical device 340. At 738, the RTSP service 2020 may transmit the RTSP stream to the hub 102 where the stream can be viewed by a health care provider.

Systems and methods for implementing medical device control in a telehealth system are described herein. In the above description, for purposes of explanation, numerous specific details were set forth. It will be apparent, however, that the disclosed technologies can be practiced without any given subset of these specific details. In other instances, structures and devices are shown in block diagram form. For example, the disclosed technologies are described in some implementations above with reference to interfaces and particular hardware. Moreover, the technologies disclosed above primarily in the context of on line services; however, the disclosed technologies apply to other data sources and other data types (e.g., collections of other resources for example images, audio, web pages).

Reference in the specification to "one embodiment," "some embodiments" or "an embodiment" means that a particular feature, structure, or characteristic described in connection with the embodiment is included in at least one embodiment of the disclosed technologies. The appearances of the phrase "in one embodiment" in various places in the specification are not necessarily all referring to the same embodiment.

Some portions of the detailed descriptions above were presented in terms of processes and symbolic representations of operations on data bits within a computer memory. A process can generally be considered a self-consistent sequence of steps leading to a result. The steps may involve physical manipulations of physical quantities. These quantities take the form of electrical or magnetic signals capable of being stored, transferred, combined, compared, and otherwise manipulated. These signals may be referred to as being in the form of bits, values, elements, symbols, characters, terms, numbers, or the like.

These and similar terms can be associated with the appropriate physical quantities and can be considered labels applied to these quantities. Unless specifically stated otherwise as apparent from the prior discussion, it is appreciated that throughout the description, discussions utilizing terms for example "processing" or "computing" or "calculating" or "determining" or "displaying" or the like, may refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The disclosed technologies may also relate to an apparatus for performing the operations herein. This apparatus may be specially constructed for the required purposes, or it may include a general-purpose computer selectively activated or reconfigured by a computer program stored in the computer.

The disclosed technologies can take the form of an entirely hardware implementation, an entirely software implementation or an implementation containing both hardware and software elements. In some implementations, the technology is implemented in software, which includes but is not limited to firmware, resident software, microcode, etc.

Furthermore, the disclosed technologies can take the form of a computer program product accessible from a non-transitory computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

A computing system or data processing system suitable for storing and/or executing program code will include at least one processor (e.g., a hardware processor) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems, and Ethernet cards are just a few of the currently available types of network adapters.

Finally, the processes and displays presented herein may not be inherently related to any particular computer or other apparatus. Various general-purpose systems may be used with programs in accordance with the teachings herein, or it may prove convenient to construct a more specialized apparatus to perform the required method steps. The required structure for a variety of these systems will appear from the description below. In addition, the disclosed technologies were not described with reference to any particular programming language. It will be appreciated that a variety of programming languages may be used to implement the teachings of the technologies as described herein.

The foregoing description of the implementations of the present techniques and technologies has been presented for the purposes of illustration and description. It is not intended to be exhaustive or to limit the present techniques and technologies to the precise form disclosed. Many modifications and variations are possible in light of the above teaching. It is intended that the scope of the present techniques and technologies be limited not by this detailed description. The present techniques and technologies may be implemented in other specific forms without departing from the spirit or essential characteristics thereof. Likewise, the particular naming and division of the modules, routines, features, attributes, methodologies and other aspects are not mandatory or significant, and the mechanisms that implement the present techniques and technologies or its features may have different names, divisions and/or formats. Furthermore, the modules, routines, features, attributes, methodologies and other aspects of the present technology can be implemented as software, hardware, firmware or any combination of the three. Also, wherever a component, an example of which is a module, is implemented as software, the component can be implemented as a standalone program, as part of a larger program, as a plurality of separate programs, as a statically or dynamically linked library, as a kernel loadable module, as a device driver, and/or in every and any other way known now or in the future in computer programming. Additionally, the present techniques and technologies are in no way limited to implementation in any specific programming language, or for any specific operating system or environment. Accordingly, the disclosure of the present techniques and technologies is intended to be illustrative, but not limiting.

What is claimed is:

1. A method comprising:
   receiving, at a node application via a server, a first real time messaging protocol message from a second application, the first real time messaging protocol message to control a medical device located at a node;
   parsing the first real time messaging protocol message;
   converting each part of the parsed first real time messaging protocol message to one or more system-level commands;
   determining whether a device driver for the medical device has been loaded;
   responsive to determining that the device driver has not been loaded,
      dynamically loading the device driver;
      converting the one or more system-level commands to a device driver command that triggers a device-specific sequence of workflow for the medical device; and
      transmitting, by the node application, the device driver command to the device driver to control the medical device for effectuating an action specified in the first real time messaging protocol message and in the sequence of workflow;
   receiving, by the node application, data from the medical device; and
   transmitting, by the node application via the server, the data from the medical device to the second application.

2. The method of claim 1, further comprising recording and storing the first real time messaging protocol message for medical auditing.

3. The method of claim 1, further comprising:
   generating a real time streaming protocol stream based on the received data from the medical device; and
   transmitting the real time streaming protocol stream to the server.

4. The method of claim 1, further comprising:
responsive to receiving the data from the medical device, generating a second real time messaging protocol message to transmit the data; and
transmitting the second real time messaging protocol message to the server.

5. The method of claim 4, further comprising transmitting the second real time messaging protocol message to the second application.

6. The method of claim 1, wherein the device driver command includes an instruction to read a configuration setting from the medical device.

7. The method of claim 6, wherein
parsing the first real time messaging protocol message includes reading the configuration setting.

8. The method of claim 1, further comprising encrypting the data from the medical device.

9. The method of claim 1, wherein the first real time messaging protocol message is transmitted through a hypertext transfer protocol tunnel.

10. A system comprising:
one or more processors; and
a memory storing instructions that, when executed by the one or more processors, cause the system to:
receive, via a server, a first real time messaging protocol message from an application, the first real time messaging protocol message to control a medical device;
parse the first real time messaging protocol message;
convert each part of the parsed first real time messaging protocol message to one or more system-level commands;
determine whether a device driver for the medical device has been loaded;
responsive to determining that the device driver has not been loaded,
dynamically load the device driver;
convert the one or more system-level commands to a device driver command that triggers a device-specific sequence of workflow for the medical device; and
transmit the device driver command to the device driver to control the medical device for effectuating an action specified in the first real time messaging protocol message and in the sequence of workflow;
receive data from the medical device; and
transmit, via the server, the data from the medical device to the application.

11. The system of claim 10, wherein the instructions, when executed by the one or more processors, cause the system to record and store the first real time messaging protocol message for medical auditing.

12. The system of claim 10, wherein the instructions, when executed by the one or more processors, cause the system to:
generate a real time streaming protocol stream based on the received data from the medical device; and
transmit the real time streaming protocol stream to the server.

13. The system of claim 10, wherein the instructions, when executed by the one or more processors, cause the system to:
responsive to receiving the data from the medical device, generate a second real time messaging protocol message to transmit the data; and
transmit the second real time messaging protocol message to the server.

14. The system of claim 13, wherein the instructions, when executed by the one or more processors, cause the system to transmit the second real time messaging protocol message to the application.

15. The system of claim 10, wherein the device driver command includes an instruction to read a configuration setting from the medical device.

16. The system of claim 15, wherein to parse the first real time messaging protocol message, the instructions, when executed by the one or more processors, cause the system to:
read the configuration setting.

17. The system of claim 10, wherein the instructions, when executed by the one or more processors, cause the system to encrypt the data from the medical device.

18. The system of claim 10, wherein the first real time messaging protocol message is transmitted through a hypertext transfer protocol tunnel.

19. A computer program product comprising a non-transitory computer usable medium including a computer readable program, wherein the computer readable program when executed on a computer causes the computer to:
receive, via a server, a first real time messaging protocol message from an application, the first real time messaging protocol message to control a medical device;
parse the first real time messaging protocol message;
convert each part of the parsed first real time messaging protocol message to one or more system-level commands;
determine whether a device driver for the medical device has been loaded;
responsive to determining that the device driver has not been loaded,
dynamically load the device driver;
convert the one or more system-level commands to a device driver command that triggers a device-specific sequence of workflow for the medical device; and
transmit the device driver command to the device driver to control the medical device for effectuating an action specified in the first real time messaging protocol message and in the sequence of workflow;
receive data from the medical device; and
transmit, via the server, the data from the medical device to the application.

20. The computer program product of claim 19, wherein the computer readable program when executed on a computer further causes the computer to:
generate a real time streaming protocol stream based on the received data from the medical device; and
transmit the real time streaming protocol stream to the server.

* * * * *